(12) United States Patent
Paulauskas et al.

(10) Patent No.: US 6,375,875 B1
(45) Date of Patent: Apr. 23, 2002

(54) DIAGNOSTIC MONITOR FOR CARBON FIBER PROCESSING

(75) Inventors: Felix L. Paulauskas; Timothy S. Bigelow; Thomas T. Meek, all of Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 09/492,473

(22) Filed: Jan. 27, 2000

(51) Int. Cl.[7] ................. B29C 47/12; B29C 47/92; C01B 31/04; D01F 9/12; G01R 27/04
(52) U.S. Cl. ............. 264/29.2; 264/29.7; 264/406; 324/636; 324/637; 324/639; 423/447.1; 423/448; 425/72.2; 425/135; 425/378.2; 425/382.2; 425/404; 425/464
(58) Field of Search ................. 264/29.2, 29.7, 264/40.1, 406, 408; 425/72.2, 135, 378.2, 382.2, 404, 464; 423/447.1, 448; 324/633, 636, 637, 639, 663

(56) References Cited

U.S. PATENT DOCUMENTS

| | | | |
|---|---|---|---|
| 4,904,928 A | 2/1990 | Lewis | 324/636 |
| 5,103,180 A | * 4/1992 | Lahitte et al. | 324/636 |
| 5,219,498 A | 6/1993 | Keller et al. | 264/408 |
| 5,268,158 A | * 12/1993 | Paul, Jr. et al. | 264/29.2 X |
| 5,334,941 A | * 8/1994 | King | 324/637 |
| 5,648,038 A | 7/1997 | Fathi et al. | 264/406 |

* cited by examiner

Primary Examiner—Leo B. Tentoni
(74) Attorney, Agent, or Firm—Akerman, Senterfitt & Eidson, P.A.

(57) ABSTRACT

A method for monitoring characteristics of materials includes placing a material in an application zone, measuring a change in at least one property value of the application zone caused by placing the material in the application zone and relating changes in the property value of the application zone caused by the material to at least one characteristic of the material An apparatus for monitoring characteristics of a material includes a measuring device for measuring a property value resulting from applying a frequency signal to the application zone after placing a material in the application zone and a processor for relating changes in the property value caused by placement of the material in the application zone to at least one desired characteristic of the material. The application zone is preferably a resonant cavity.

20 Claims, 14 Drawing Sheets

| Sample No. | Dielectric Properties | Tan δ | ε" | Intrinsic Density gr/cc | Calcualated Tow Area (50K), cm² |
|---|---|---|---|---|---|
| 1 | Low Loss | 0.0221 | 0.1056 | 1.4126 | 0.05356 |
| 2 | High Loss | 0.9481 | 4.4217 | 1.4290 | 0.05049 |
| 3 | Low Loss | 0.0222 | 0.1089 | 1.4210 | 0.05132 |
| 4 | High Loss | 0.4711 | 2.8067 | 1.4364 | 0.05131 |
| 5 | Low Loss | 0.0221 | 0.1077 | 1.3946 | 0.05270 |
| 6 | High Loss | 1.1379 | 6.2839 | 1.4376 | 0.05290 |
| 7 | Low Loss | 0.0216 | 0.1048 | 1.4343 | 0.05241 |
| 8 | High Loss | 0.0739 | 0.4072 | 1.4589 | 0.05198 |
| Observed Average | | 0.0300 | 0.1511 | 1.4281 Calculated Average | 0.05208 Calculated Average |

| Sample No. | Dielectric Properties | Tan δ | ε" | Intrinsic Density gr/cc | Calcualated Tow Area (50K), cm² |
|---|---|---|---|---|---|
| 1 | Generic Point | 0.0622 | 0.5556 | 1.6872 | 0.3446 |
| 2 | Low Loss | 0.0541 | 0.4541 | 1.6561 | 0.03520 |
| 3 | High Loss | 0.2428 | 2.6072 | 1.6545 | 0.03585 |
| 4 | High Loss | 0.2345 | 2.2771 | 1.6606 | 0.03293 |
| 5 | Low Loss | 0.0507 | 0.411 | 1.6877 | 0.03412 |
| 6 | High Loss | 0.1822 | 1.7502 | 1.6941 | 0.03566 |
| 7 | Low Loss | 0.0489 | 0.3985 | 1.6859 | 0.03459 |
| 8 | High Loss | 0.3037 | 2.6485 | 1.6944 | 0.03543 |
| 9 | Low Loss | 0.0496 | 0.3998 | 1.6885 | 0.03494 |
| Observed Average | | 0.0539 | 0.4207 | 1.6788 Calculated Average | 0.03480 Calculated Average |

Dielectric Properties Of Commercial Grade
Glass-Fiber/Epoxy Reinforced Composite (GFRC)
Using The Resonance Cavity Method At 2.44 GHz and 25°C
As A Function Of The Moisture Content

| GFRC Processing | $\varepsilon'$ | Tan $\delta$ |
|---|---|---|
| None (As Received) | 4.68 | 0.0161 |
| Oven Dried At 101°C In Vacuum For 90 Hrs. | 4.46 | 0.0136 |

*FIG. 13*

DIAGNOSTIC MONITOR FOR CARBON FIBER PROCESSING

The U.S. Government has a paid-up license in this invention and the right in limited circumstances to require the patent owner to license others on reasonable terms as provided for by the terms of Contract No. De-AC05-960R22464 awarded by the U.S. Department of Energy to Lockheed Martin Energy Research Corporation.

CROSS REFERENCE TO RELATED APPLICATIONS (Not Applicable)

STATEMENT REGARDING FEDERALLY SPONSORED RESEARCH OR DEVELOPMENT

BACKGROUND OF THE INVENTION

1. Field of the Invention

The invention relates to an apparatus and method for measuring the properties of materials. More specifically, the invention relates to an apparatus and method for the in situ, real-time monitoring and control of properties and characteristics of a material.

2. Description of the Relevant Art

For at least the last four decades, carbon fibers have been used as a substitute for steel, aluminum, titanium, and glass fibers, among others. Carbon fibers are an ideal material for use in a wide range of applications due to their strength and stiffness, light weight, high fatigue resistance and vibration damping, corrosion resistance, good friction and wear qualities, low thermal expansion, and thermal and electrical conductivity. Thus, fabrication and design using carbon fibers offers a degree of versatility that is not available when using other materials.

Carbon fibers are manufactured conventionally through the controlled pyrolysis, or chemical change through heating, of a precursor material. This precursor material includes rayon (or regenerated cellulose) fibers, pitch (petroleum and coal-tar)-based fibers, and polyacrylonitrile (PAN) fibers, among others. This pyrolysis has continuous sequential process stages, and each process stage is identified by a unique set of process conditions. Carbon fibers are manufactured to certain specifications, which are dependent on their ultimate use. The transformation of precursor materials to carbon fibers during the manufacturing process must be monitored in some way to ensure that these specifications are met. Current quality control of carbon fiber manufacturing is limited to non-real time analysis. These current quality control methods require the physical removal of a sample from the carbon fiber after the completion of each specific process stage. These samples are then taken to a laboratory for determining whether that carbon fiber falls within its required specification range (e.g., density, electrical resistivity, mechanical strength, etc.). Once an analysis of the sample is made, process control decisions are made to either maintain the process, or to regulate the process and bring the unprocessed precursor material into the desired specification range.

This current quality control method is both time consuming and inefficient. In general, a carbon fiber production line consists of multiple carbon fiber tows (or strands—up to around 300), being produced at a linear processing speed up to approximately 1 linear foot per second depending on specific products and their quality specifications. There is a considerable passage of time (from 0.5 to 3 hours) between the initial removal of carbon fiber samples from the production line and any necessary changes which need to be made to the production process to ensure that future tows fall within the desired specification range.

Thus, the time spent sampling and analyzing processed carbon fibers results in the production of quantities of carbon fibers that fall outside of the desired specification range. These unacceptable carbon fibers are then either fully rejected or diverted to a secondary market, resulting in either an absolute loss or reduction of profit to the carbon fiber producer (and transitively a high cost to the end user of those carbon fibers that do fall within a desired specification range). It is therefore desirable to be able to perform real-time monitoring for unacceptable carbon fibers during the production process, so that a producer can immediately determine whether the properties of a given carbon fiber tow fall within a desired specification range. Such immediate knowledge allows the producer to modify the production process earlier, resulting in the reduced production of unacceptable carbon fibers.

Although microwave energy has not been used to make in situ, real-time measurements of the properties of carbon fiber tows during their production, it has been used to measure the properties of various other materials. For example, U.S. Pat. No. 5,648,038 to Fathi et al. discloses the use of microwave energy to measure an entire material inside a chamber by generating variable frequency microwave energy and using the detected power reflection for each one of the generated variable frequencies to determine certain properties of that material. Fathi et al. does not disclose the use of microwave signals to measure the dielectric properties of a given material, rather it discloses the measurement of the reflection of microwave signals generated in a microwave cavity. Furthermore, Fathi et al. defines measurement as occurring in a microwave cavity having multiple modes, which requires sweeping over a wideband frequency range in order to achieve uniformity in the measurement of the desired material.

Another example of the use of microwave energy to measure material properties is disclosed in U.S. Pat. No. 4,904,928 to Lewis. Lewis discloses the measuring of material properties through the difference of the frequency of oscillation of least two identical resonant modes having substantially the same resonant frequencies but orthogonal field orientations relative to one another as those modes are oscillating in a symmetrical microwave cavity. Lewis discloses the geometrical (diameter) measurement of a given material by monitoring changes in frequency separation between modes which are by variations in amount of the low loss dielectric material present. Lewis does not disclose the measurements of possible variations in the fiber diameter by monitoring changes in the transmitted signal level.

An example of the measurement of the dielectric properties of a material is disclosed in U.S. Pat. No. 5,219,498 to Keller et al. Keller et al. discloses the use of a low frequency signals and measures capacitance and dielectric loss between metallic electrodes embedded in the composite matrix of the measured resins or composites. Keller et al. does not disclose the measurement of the dielectric properties of a material without the use of an embedded metallic electrode, such as by a microwave signal.

Thus, none of these references address the problem of using a resonance cavity to determine the dielectric properties of a given carbon fiber tow in order to monitor changes in the specific degree of carbonization or graphitization characteristics of that carbon fiber tow during it production process.

BRIEF SUMMARY OF THE INVENTION

It is an object of the invention to provide an apparatus and a method for monitoring the purity of a material composition.

It is an object of the invention to provide an apparatus and a method for monitoring the quality of a material composition.

It is an object of the invention to provide an apparatus and a method for monitoring the composition of a material composition.

It is an object of the invention to provide an apparatus and a method for monitoring the moisture content of a material composition.

It is an object of the invention to provide an apparatus and a method for the in situ, real-time monitoring of the carbon fiber production process.

It is another object of the invention to provide an apparatus and a method for the in situ, real-time control of the carbon fiber production process.

It is still another object of the invention to provide a method and apparatus for producing carbon fiber tows falling within a given specification range that consumes a reduced amount of precursor material.

It is yet another object of the invention to provide a method and apparatus for producing carbon fiber tows falling within a given specification range in a manner consuming reduced resources, including time and energy, among other things.

It is a further object of the invention to provide a method and apparatus for using microwave energy to measure the properties of a carbon fiber tow during the production process.

It is still a further object of the invention to provide a method and apparatus for using microwave energy to monitor the properties of a carbon fiber tow during the production process.

It is an additional object of the invention to provide a method and apparatus for using microwave energy to control the properties of a carbon fiber tow during the production process.

These and other objects of the invention are achieved by the subject method which comprises applying a frequency signal, such as microwave or RF energy, to make an in situ, real-time measurement of the properties of a material composition, such as a carbon fiber tow, during or after the production of the material. The step of measuring the properties of the material composition can be accomplished in any manner and includes applying the frequency signal, such as microwave or RF energy, to a measurement applicator, such as a resonance cavity or a parallel plate dielectric measurement device, placing or continuously feeding the material composition, such as the carbon fiber tow, in or through the resonance cavity, measuring changes in the microwave field applied to the resonance cavity caused by the portion of material composition present in the resonance cavity, and relating the changes in the microwave field applied to the resonance cavity caused by the portion of material composition, such as the carbon fiber tow, present in the resonance cavity to properties of that portion of material composition, such as purity, composition, moisture content or fiber density, among others.

The microwave energy applied to the resonance cavity, and to the material composition fed through the resonance cavity, should be of low enough power to prevent changes in the structure of the material composition being monitored. For example, when the material composition is a carbon fiber tow, the microwave energy applied to the resonance cavity should be of low enough power to allow for the continued oxidation, carbonization or graphitization of the carbon fiber tow. The microwave or RF band energy applied to the resonance cavity preferably has a fixed frequency. Also, the resonance cavity preferably has a single mode.

Any intrinsic property related to the moisture content, purity, composition or absorptivity of the material composition, and specifically any changes or variations of these properties, along the length of the monitored material composition can be selected to measure the characteristics of the material composition. For example, absorptivity can be related to the specific, well defined state of a carbon fiber tow during its processing. Furthermore, the association between the values of any purity, moisture content, composition or absorptive intrinsic property of the monitored material composition, such as the loss tangent of the material composition, and the moisture, purity, composition or morphology of the material composition must be known. These associating values may be formulated into a baseline containing the interrelation between any of the dielectric properties of the material compositions, such as the loss tangent of the material composition, and the corresponding characteristics of the material composition, such as the purity, composition or morphology (i.e., intrinsic density), among other characteristics.

In another embodiment of the present invention, an apparatus for monitoring properties or characteristics of materials is disclosed. This apparatus includes an applicator for applying a frequency signal to an application zone; a placement device for placing a material in the application zone; a measurer for measuring a property value resulting from said applicator applying the frequency signal to the application zone prior to said placement device placing the material in the application zone and for measuring changes in the property value of the application zone caused by said placement device placing the material in the application zone; and a processor for relating said changes in the property value of the application zone caused by said placement device placing the material in the application zone to a desired characteristic of the material. The placement device can also be a feeder that feeds the material through the application zone. When the feeder is used, the measurer continuously measures the property values of the portions of material being fed through the application zone.

According to another embodiment of the invention, an apparatus for producing carbon fibers may comprise a precursor filament transport for transporting a precursor filament through the carbon fiber production process; a pretreater for preparing the precursor material for the oxidation process; an oxidizer for inducing the stabilization and oxidation of the precursor filament; a carbonizer for inducing the carbonization of an oxidized precursor filament into carbon filaments; a graphitizer for inducing the graphitization of the carbon filaments; a treater for treating the surface of the carbon fibers which have graphitized; a post-production device for sizing and/or drying produced carbon fiber tows; a packager for packaging the carbon fibers; and a material composition monitor for monitoring the morphology of a filament during the carbon fiber production process. The transport need not continuously transport the precursor filament through the carbon fiber production process; the process can be incremental or performed in batches.

In this embodiment of the invention, the material composition monitor comprises a measurement applicator, such as a resonant cavity among other things, in which certain measurements, such as changes in dielectric properties, can be made; a carbon fiber tow which is placed or continuously fed through the resonance cavity; a signal generator for applying frequency signals, such as microwave energy, through a device, such as a waveguide or coaxial cable, to the measurement applicator; and a microwave measuring device connected to the resonance cavity. Preferably, the material composition monitor also comprises a processor for correlating the output of the microwave measuring device to the corresponding characteristics of the carbon fiber tow which is placed in, or fed through, the resonance cavity.

In the present invention, the measurement apparatus is preferably a resonance cavity. The microwave measuring device measures the changes in frequency signal, which is preferably a microwave field, applied to the resonance cavity caused by the placing or continuous feeding of the portion of the carbon fiber tow through the resonance cavity. In the present invention, the change in the microwave field applied to the resonance cavity is preferably the change in the electric quality factor (Q) of the resonance cavity. In the present invention, the resonance cavity is preferably an empty resonance cavity with a known electric quality factor. In the present invention, the processor preferably correlates the change in the electric quality factor of the resonance cavity caused by the continuous feeding of the carbon fiber tow through the resonance cavity to the characteristics of the carbon fiber tow, such as intrinsic density, among others.

BRIEF DESCRIPTION OF THE DRAWINGS

There are shown in the drawings embodiments of the invention that are presently preferred. It being understood, however, that the invention is not limited to the precise arrangements and instrumentalities shown, wherein:

FIG. 4 is a table illustrating the correlation between the dielectric properties of different portions of a fully oxidized PAN-based carbon fiber tow and the intrinsic density and calculated area of those different portions of fully oxidized PAN-based carbon fiber tow.

FIG. 9 is a table illustrating the correlation between the dielectric properties of different portions of a carbonized PAN-based carbon fiber tow and the intrinsic density and calculated area of those different portions of carbonized PAN-based carbon fiber tow.

FIG. 13 is a table illustrating the correlation between the dielectric properties of a glass-fiber/epoxy reinforced composite and the moisture content of that composite.

DETAILED DESCRIPTION OF THE PREFERRED EMBODIMENTS

Figure 1:
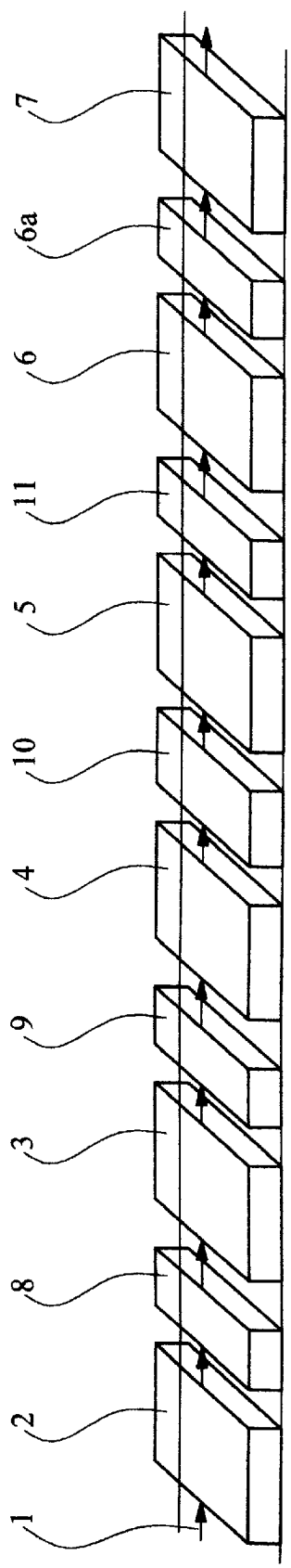
FIG. 1 illustrates the preferred embodiment of an apparatus for monitoring and/or controlling the production of a carbon fiber tow according to the present invention.

Referring to FIG. 1, an apparatus for producing carbon fibers, according to a the present invention, is illustrated. The apparatus comprises a precursor filament transport 1 for transporting a precursor material through the carbon fiber production proceeds a pretreater 2 for preparing the precursor filament for the production process; an oxidizer 3 for inducing the stabilization and oxidation of the precursor filament; a carbonizer 4 for inducing the carbonization of an oxidized precursor filament into carbon filaments; a graphitizer 5 for inducing the graphitization of the carbon filaments; a treater 6 for treating the surface of a carbon fibers which have been graphitized; a post-production device 6a for sizing and drying the graphitized carbon fibers; a packager 7 for packaging the carbon fibers; and one or more material composition monitors 8 through 11 for monitoring the morphology of a filament at a given point during the carbon fiber production process.

The present embodiment of the invention is suitable for the production of any fiber based filament production. This embodiment of the present invention is an example of current fiber technology. However, this apparatus can work with any technology for the manufacturing of carbon fiber tows.

The precursor filament transport 1 has no required transport mechanism. It must only be able to transport the precursor filament through each stage of the carbon fiber production process at a rate necessary for the characteristics of a produced carbon fiber to fall within a given specification range. It is currently preferred that the precursor filament transport 1 transports bundles of precursor material having a diameter or band width of around 5 inches. These bundles of precursor material include around 200,000 individual precursor filaments. In addition to being wide enough to transport the amount of precursor filaments necessary to form a full carbon fiber tow, the precursor filament transport 1 must also be long enough to transport the precursor filaments through element of the production line so that a completed carbon fiber tow can be produced. Typically, this length is around one quarter of a mile or longer.

The pretreater 2 extrudes a polymer solution or melt into the fine precursor filaments that are used in the production process. In doing so, the pretreater washes, heats and stretches the polymer solution or melt into an end product precursor filament, which is then enters the carbonization process. Such a pretreater 2 is commonly used in all carbon fiber production.

The oxidizer 3 stabilizes the precursor filament, preparing the precursor filament for carbonization. The oxidizer 3 subjects the precursor filament to relatively low temperatures of around 200–450° C., usually in air. This converts the precursor filament to an infusible state, and makes it stable for subsequent higher temperature processing.

The carbonizer 4 subjects the filament to temperatures around 1000–2000° C. The carbonizer 4 usually has an inert atmosphere. For instance, the carbonizer 4 can be filled with pure nitrogen. The carbonizer 4 generally increases the carbon content of the precursor filament to around 85–99% of the weight of the carbonized precursor filament.

The graphitizer 5 causes graphitization of the carbon fiber which is produced by the carbonizer 4. The graphitizer 5 subjects the carbon fiber to temperatures generally in excess of 2500° C. The graphitizer 5 usually has an inert atmosphere. For instance, the graphitizer 5 can be filled with Ar or $N_2$. The graphitizer 5 generally increases the carbon content of the carbon fiber to greater than 99%.

The surface treater 6 treats the surface of the graphitized carbon fiber to promote adhesion to a matrix. For instance, the surface treater 6 allows the carbon fiber to adhere better to a polymeric resin, among others.

The post-production device 6a prepares the graphitized carbon fiber tows for commercial sale or use, among other things. Two examples of the preparation performed by the post-production device 6a are the drying and/or sizing of the graphitized carbon fiber tows. Other forms of preparation of the produced carbon fiber tows may, however, be performed.

The packager 7 packages the produced carbon fibers so that they may be more easily stored and transported. One possible example of the packager is a spooler which spools the processed carbon fiber.

Figure 2:
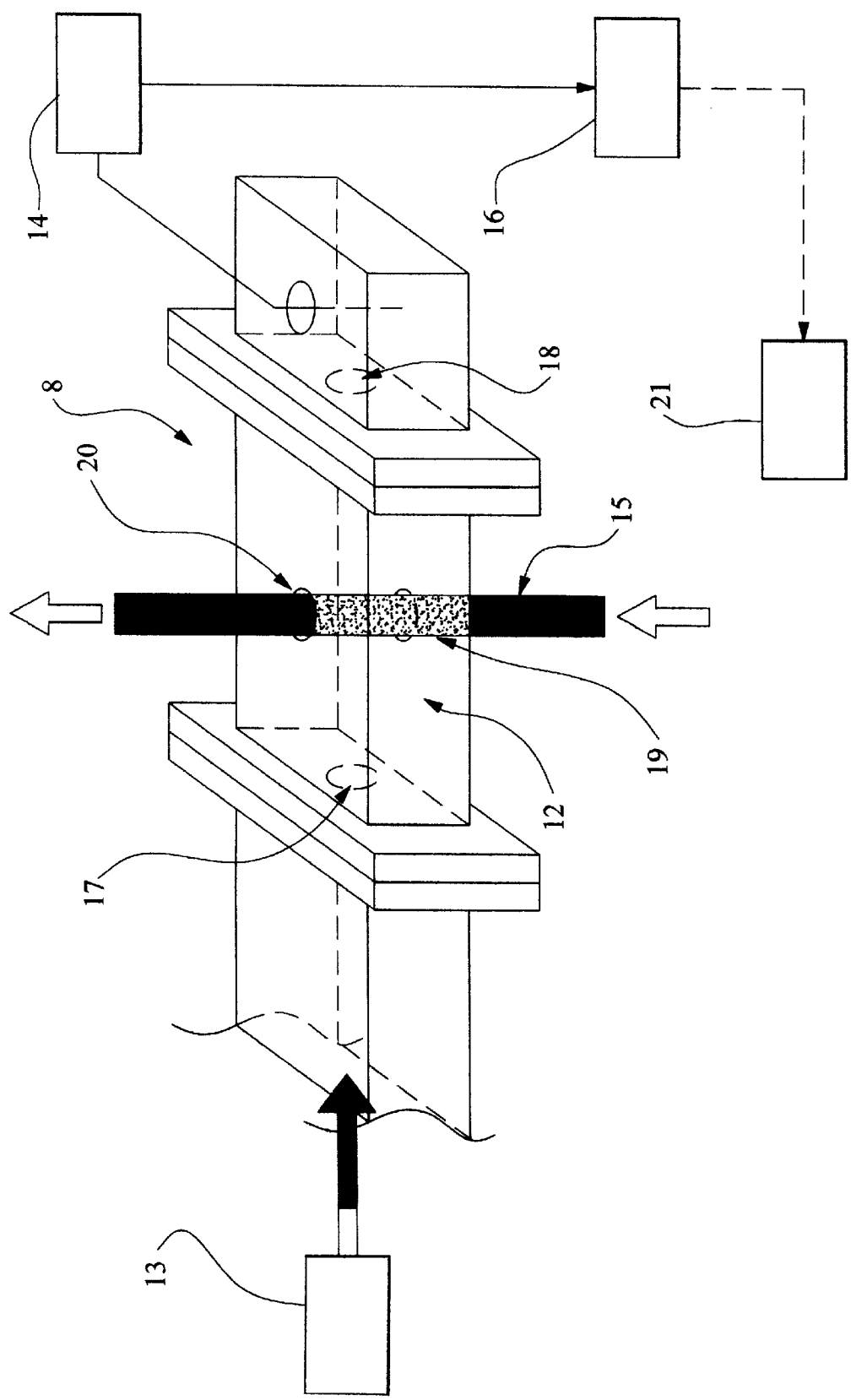
FIG. 2 illustrates the preferred embodiment of a material composition monitor for use in the present invention.

Referring to FIG. 2, the material composition monitor 8, according to the present invention, is illustrated. This material composition monitor 8 can be used in conjunction with the apparatus illustrated in FIG. 1 or as a standalone unit. The material composition monitor 8 contains an measurement applicator, such as a parallel plate dielectric measurement device or a resonance cavity 12, among other things, for providing an area in which to measure certain properties, such as the dielectric characteristics, of a given material; a signal generator 13 for applying a frequency signal, such as microwave or RF energy, to the resonance cavity 12; and a microwave measuring device 14 for continuously measuring the changes in the microwave field applied to the resonance cavity 12, such as changes in the electric quality factor (Q), caused by the feeding a material composition, such as the carbon fiber tow 15, through the resonance cavity 12. It is also preferred that the present invention comprise a processor 16 for correlating the changes in the microwave field applied to the resonance cavity 12, such as changes in the electric quality factor (Q), caused by the portion of material composition resident in the resonance cavity 12 to the corresponding characteristics of that portion of material composition.

According to the present invention, the material composition monitor 8 may also comprise a controller 21 for controlling the characteristics, such as the moisture content, of the material compositions being fed through the resonance cavity 12, or for controlling the carbon fiber production process based on the characteristics of the carbon fiber tow 15 being fed through the resonance cavity 12. This controller 21 can be a computer and/or a closed feedback loop, among other things. For instance, when controlling the carbon fiber production process, this computer may be used to raise or lower the temperature in different steps of the production process if the portion of the carbon fiber tow fed through the resonance cavity does not fall within a given specification range. When controlling the moisture content of other material compositions, this computer may be used to raise the oven temperature at which the material compositions are being dried in order to have the material compositions fall within a specific moisture range.

The material composition monitor 8 is not limited to any specific measurement applicator. The measurement applicator need only be an area in which certain measurements, such as electric quality factor (Q) or dielectric properties, can be made. In the present invention, the measurement applicator is preferably a resonance cavity 12. The resonance cavity 12 may be separated and moved, allowing for the resonance cavity 12 to be moved from material composition to material composition with ease. For example, when the present invention is during the carbon fiber production process, it is preferable that the resonance cavity 12 be able to be opened and moved from the carbon fiber tow 15 to a different carbon fiber tow, wherein the resonance cavity 12 can then be closed around the different carbon fiber tow. By easily opening and closing the resonance cavity 12, the material composition monitor 8 can monitor and/or measure the properties of multiple carbon fiber tows during the production process. When the resonance cavity 12 can be separated and moved, special consideration must be made to construct this resonance cavity 12 so that there is a minimal amount of leakage of the electromagnetic field found in the resonance cavity 12, as such leakage will result in reduced sensitivity of the resonance cavity 12 for the measurement of properties of the material compositions being measured.

The material composition monitor 8 is not limited to any specific signal generator 13. Any commercial generator can be used. However, it is currently preferred that the signal generator 13 generate a signal frequency in the microwave band. The use of microwave frequencies offer improve sensitivity, and possibly a more convenient measurement method, than alternative signal frequency. The signal generator 13 need not have the capacity to sweep or vary the signals applied to the measurement applicator. A fixed signal generator can also be used. For example, the signal generator 13 may be a Gunn Diode or dielectric resonator/oscillator. In the present invention, a network analyzer with a built-in signal generator is the preferred signal generator 13 in the material composition monitor 8.

The material composition monitor 8 is not limited as to the amount or duration of the frequency signal, such as the microwave or RF energy, applied. Any combination of the amount or duration is acceptable as long as the change in the microwave field applied by the signal generator 13 to the resonance cavity 12, such as the change in the electric quality factor (Q), can be measured. The signal generator 13 need only apply a microwave with sufficient power to provide adequate signal levels to the microwave measuring device 14. Preferably, the amount or power of the microwave energy applied to the resonance cavity 12 will be low enough to prevent changes in the structure of the material composition being monitored. For example, when the material composition being monitored is the carbon fiber tow 15, the microwave energy applied to the resonance cavity should be of low enough power to prevent the continued oxidation, carbonization or graphitization of the carbon fiber tow 15 found therein. In the present invention, the preferred amount of microwave energy applied to the resonance cavity 12 in the material composition monitor 8 is about 10 mW.

The frequency of the microwave energy applied in the material composition monitor 8 can be either fixed or variable and is not limited as to a particular frequency or frequency range. Any frequency that can be used to measure the changes in the microwave field applied to the resonance cavity 12, such as changes in the electric quality factor (Q), can be used. The frequency of the microwave should be such that the resonance cavity 12 to which it is applied functions as a single mode resonance cavity. Although any microwave or RF frequency can be applied to the resonance cavity 12, a lower microwave frequency, such as and S-Band frequency in the range of 2 GHz to 4 GHz, is presently preferred in the material composition monitor 8.

The frequency of the microwave energy applied in the material composition monitor 8 will determine the type and size of the measurement applicator to be used, or vice versa. Generally, any type of resonance cavity can be used. However, it is presently preferred that the resonance cavity 12 be rectangular in shape, as it is the simplest and easiest to interpret. In addition, there is no restriction as to the amount of modes that the resonance cavity in the material composition monitor 8 may have. Although there is no restriction on the amount of modes that the resonance cavity 12 may have, a single mode resonance cavity is presently preferred for use in the embodiment of the material composition monitor 8 illustrated in FIG. 2. Use of a single mode resonance cavity is preferred because of the complication that the excitement of additional modes adds to measuring changes in the microwave field applied to the resonance cavity 12, such as changes in the electric quality factor (Q), caused by the portion of material composition, such as carbon fiber tow 15, present in the resonance cavity 12.

A resonance cavity has a single mode when the length and width of that resonance cavity are equivalent to one-half of the wavelength of the applied microwave, and the height of that resonance cavity is much smaller in size than the length and width, such as one quarter of the wavelength of the applied microwave. Therefore, the wavelength and, subsequently, the dimensions of that resonance cavity are dictated by the frequency of the applied wave, and vice versa. The relation of the wavelength of the microwave to its frequency is:

$$\lambda = (3 \times 10^8)/f$$

In addition, the dimensions of the resonance cavity can be determined using the equation:

$$f_o = (1.5 \times 10^8)\sqrt{1/a^2 + 1/d^2_1}$$

where $f_o$ is the resonance frequency, or the microwave field applied by the signal generator 13, a is the width of the resonance cavity, and d is the length of the resonance cavity.

Thus, if a very high frequency wave is generated by the signal generator 13, the size of the resonance cavity 12 will be very small in order for that resonance cavity 12 to have a single mode. Such a small resonance cavity 12 would be difficult to feed most material compositions through, among other things. For example, it would be extremely difficult for an average size carbon fiber tow to be passed through such a small resonance cavity. Conversely, if a very low frequency wave is generated by the signal generator 13, the size of the resonance cavity 12 will be very large in order for that resonance cavity 12 to have a single mode. Such a resonance cavity would consume a large amount of space in, for example, a carbon fiber production line, among other things. Thus, in the present invention, a signal generator 13 which generates a microwave band signal is preferred.

The resonance cavity 12 used in the material composition monitor 8 can be made from a wide variety of metals. In general, a metal with a high electric quality factor (Q), such as copper or aluminum, is presently preferred. However, if the resonance cavity 12 is placed in a high temperature environment, such as an environment having a temperature of around 900° C. or higher, the resonance cavity 12 may need to be constructed from a metal such as tantalum, tungsten, etc. In these high temperature environments, special consideration in the design and construction of the resonance cavity 12 should be taken depending on the presence of oxygen. The resonance cavity 12 should not be constructed of any material that will oxidize in the environment in which it is used, as such oxidation will cause surface conductivity, and therefore, the electric quality factor (Q), of the resonance cavity 12 will change. Such a change can cause an improper measurement of the change in the electric quality factor (Q) as a function of the portion of carbon fiber tow 15 fed through the resonance cavity 12. If the resonance cavity 12 is placed in a high temperature environment, the resonance cavity 12 can be calibrated for use in the present invention by measuring the electric quality factor (Q) of the resonance cavity 12 while it is empty as a function of temperature over the desired temperature range. In the present invention, it is preferred that the resonance cavity 12 be placed in a stable temperature, so that recalibration of the cavity is not required. Once these measurements are made, the resonance cavity 12 can then be used for measuring the dielectric properties of the portion of material composition, such as the carbon fiber tow 15, found in the resonance cavity 12 within that temperature range.

A first coupling iris 17 and second coupling iris 18 located on opposite sides of the resonance cavity 12 should each have a diameter small enough to prevent a reduction in the electric quality factor (Q) of the resonance cavity 12. In general, the first coupling iris 17 and the second coupling iris 18 should each have areas no greater than about ten percent of the total areas of the sides of the resonance cavity 12 on which they are found are presently preferred in the material composition monitor 8. A material composition entry hole 19 and a material composition exit hole 20, located on opposing sides of the resonance cavity 12, should allow the material composition, such as the carbon fiber tow 15, to pass through the resonance cavity 12 or the center of the resonance cavity 12. For example, the material composition entry hole 19 and the material composition exit hole 20 can be located on the bottom and top of the resonance cavity 12, respectively. The material composition entry hole 19 and material composition exit hole 20 should also be restricted in size so as not to cause any change in the microwave energy being applied to the resonance cavity 12. However, the material composition entry hole 19 and the material composition exit hole 20 should be large enough so that the material composition, such as the carbon fiber tow 15, being fed through the material composition entry hole 19 and the material composition exit hole 20 is not caused to bind up and impede movement through the present invention. In general, the diameters of the material composition entry hole 19 and the material composition exit hole 20 should fall within a range equivalent to 0.1% to 10% of the area of the top and bottom of the resonance cavity 12, respectively, depending on the diameter of the material composition being monitored. Additionally, the diameters of the material composition entry hole 19 and the material composition exit hole 20 will preferably be less than about 5% of the width of the top and bottom of the resonance cavity 12, respectively, in order to minimize signal loss and the perturbing of any fields, such as microwave fields, in the resonance cavity 12 while it is empty.

The material composition entry hole 19 and the material composition exit hole 20 can be placed anywhere on the bottom and top of the resonance cavity 12, respectively. However, the resonance cavity 12 is most sensitive at its center, where the electric field of the cavity is maximum. The center of the cavity is therefore the easiest point at which to get a meaningful relationship between the frequency shift caused by the transport of a portion of the material composition, such as the carbon fiber tow 15, through the resonance cavity 12 and the dielectric properties of that portion of material composition. As such, in the material composition monitor 8, placement of the material composition entry hole 19 and material composition exit hole 20 is preferred at the center of each of opposing sides of the resonance cavity 12. If these material composition entry and exit holes are placed in another location on the bottom and top of the resonance cavity, respectively, the measurements of the change in the electric quality factor (Q) of the resonance cavity caused by the transport of portion of a material composition through the resonance cavity will be less sensitive and will require a correction factor due to the reduction of electric field levels when moving away from the center of the resonance cavity.

The microwave measuring device 14 is any device capable of measuring a microwave field. The microwave measuring device 14 is used to monitor variations in signal levels of the microwave field applied to the resonance cavity 12. In the present invention, the microwave measuring device 14 is preferably a microwave detector or a network analyzer.

The processor 16 is not restricted in the manner in which it correlates these changes in the microwave field applied to the resonance cavity 12 to the corresponding characteristics of the portion of the material composition, such as the carbon fiber tow 15, passing through the resonance cavity 12. It is presently preferred that the processor 16 associate the change in the electric quality factor (Q) of the resonance cavity 12 caused by the portion of material composition, such as the carbon fiber tow 15, resident in the resonance cavity 12 to the loss tangent of that portion of material composition. It is also presently preferred that the loss tangent of that portion of material composition then be related to the characteristics of that portion of material composition, such as its moisture content, purity, composition. If the material composition is the carbon fiber tow 15, these related characteristics can include, among other things, intrinsic density, mechanical strength, or ultimate strength.

Figure 3:
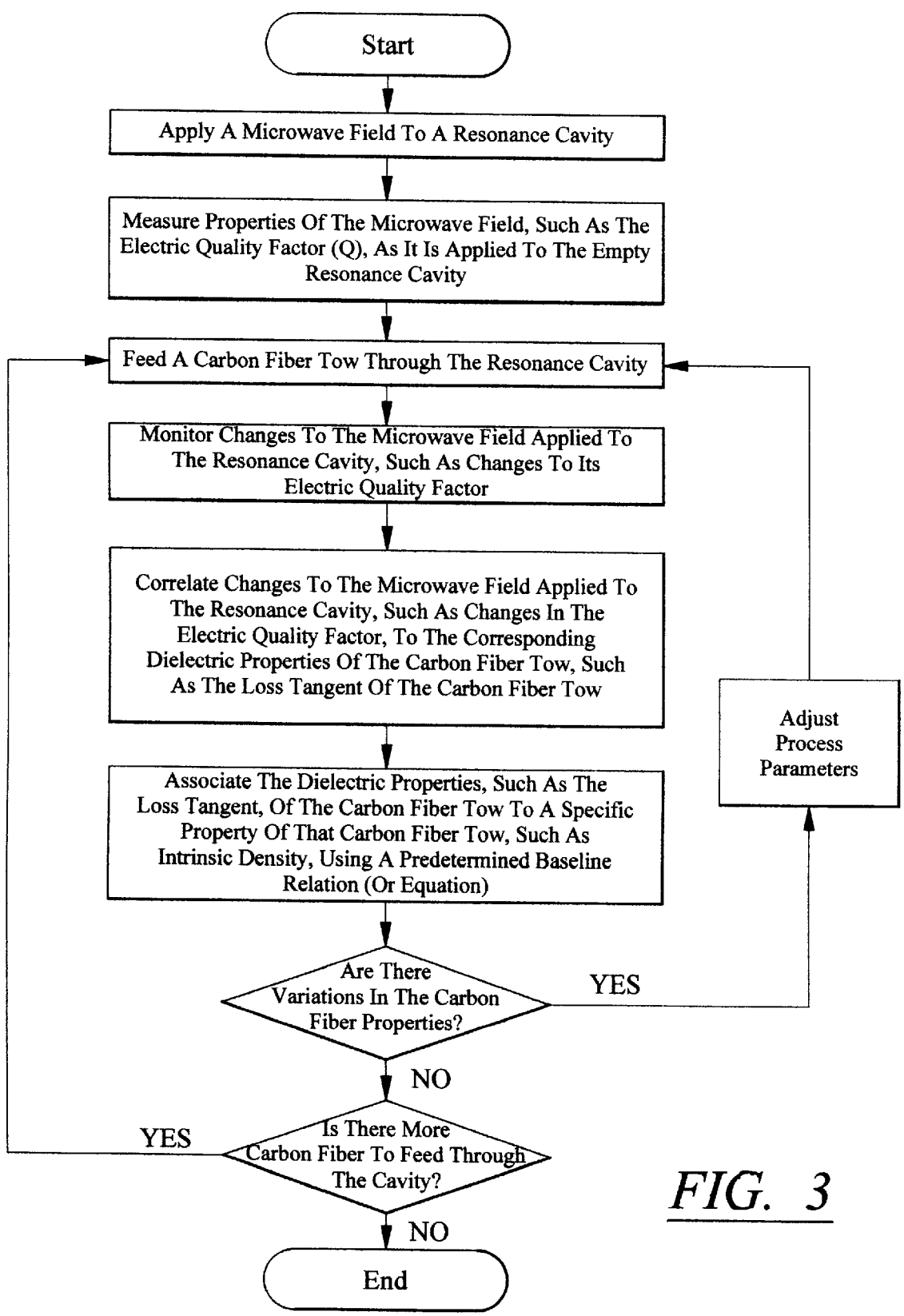
FIG. 3 is a flow diagram illustrating method steps according to a preferred embodiment of the present invention.
Figure 5:
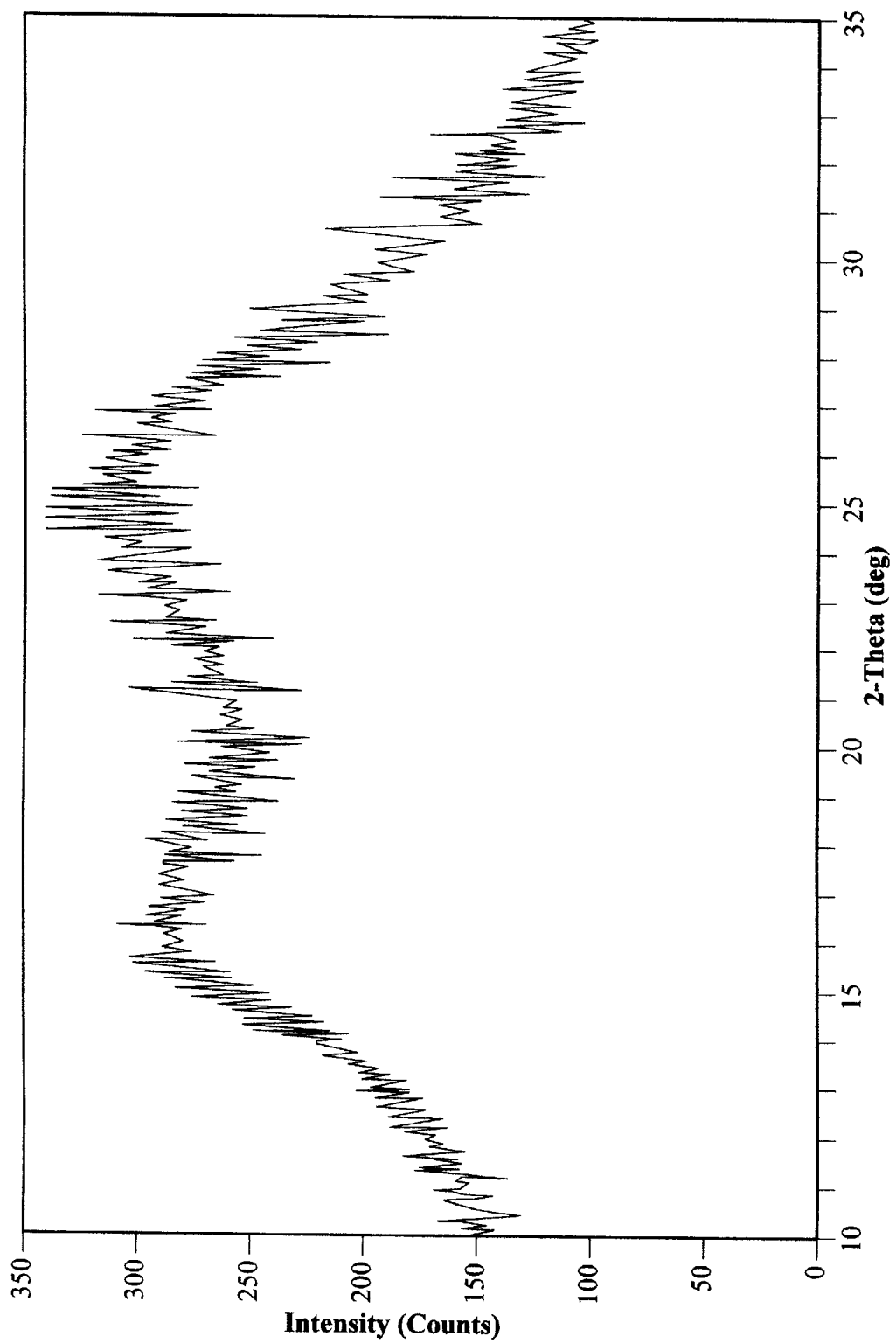
FIG. 5 is an x-ray diffractogram illustrating the intensity of a high lossy length of fully oxidized carbon fiber.
Figure 6:
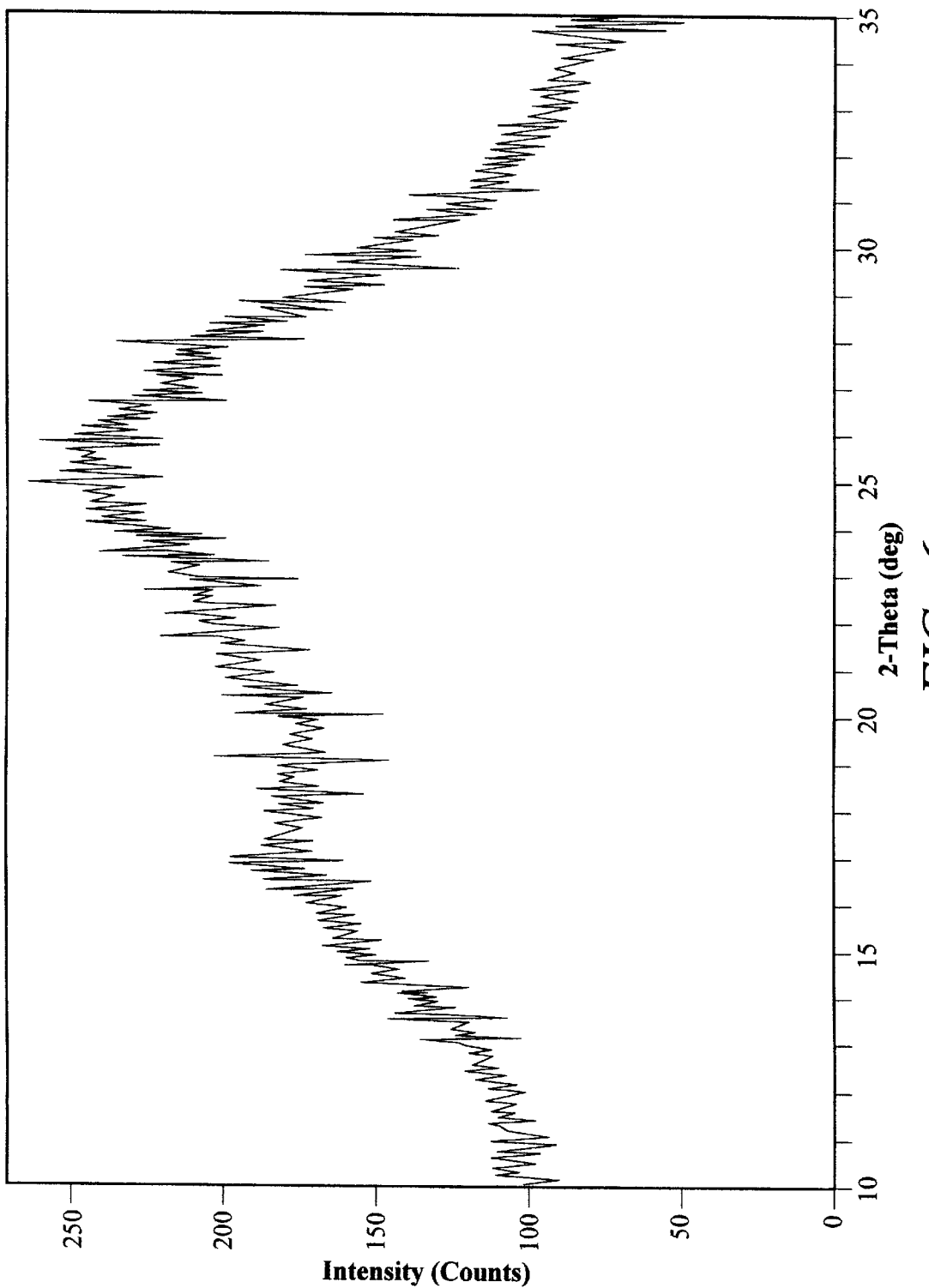
FIG. 6 is an x-ray diffractogram illustrating the intensity of a low lossy length of fully oxidized carbon fiber.
Figure 7:
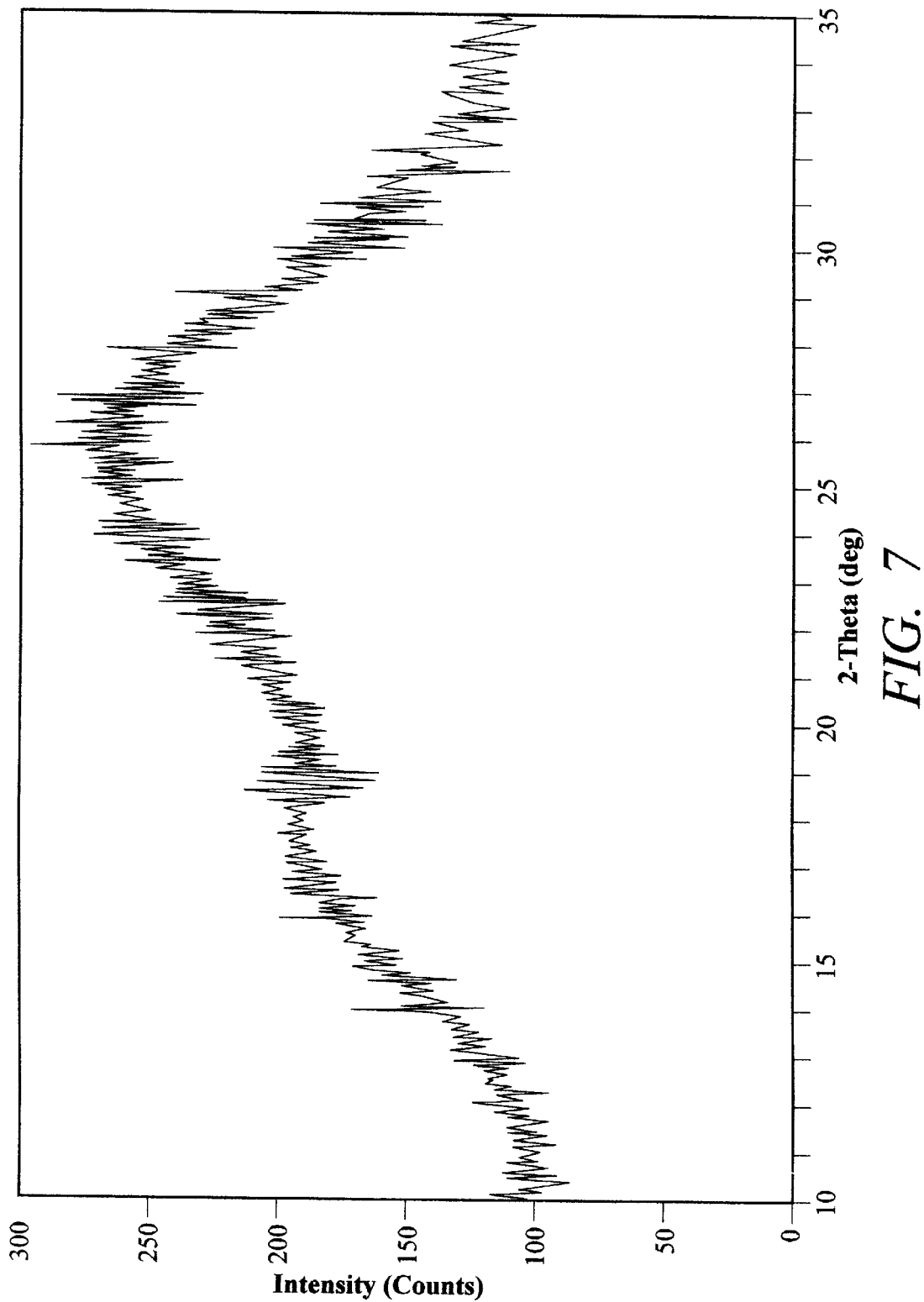
FIG. 7 is an x-ray diffractogram illustrating the intensity of a moderately lossy length of fully oxidized carbon fiber.

Referring to FIG. 3, a method for monitoring the characteristics of a material composition, according to the present invention, is shown. The method comprises applying a microwave field to an empty resonance cavity; measuring properties of the microwave field, such as the electric quality factor (Q), of the empty resonance cavity; placing a material composition in the resonance cavity; monitoring changes in the microwave field applied to the resonance cavity, such as changes in the electric quality factor (Q); correlating the changes in the microwave field applied to the resonance cavity, such as changes in the electric quality factor (Q), to the corresponding dielectric properties of the material composition, such as the loss tangent of the material composition, among other things; and associating the dielectric properties of the material composition, such as the loss tangent of the material composition, to a specific property of that material composition, such as the moisture content, purity, composition, intrinsic density, mechanical weight, or ultimate strength, among other things, of that material composition, using a predetermined baseline relation (or equation). In the present invention, the material composition can also be continuously fed through the resonance cavity. In the present invention, the material composition composed monitored can be a carbon fiber tow, among other things.

This method for monitoring characteristics of the material composition can include, for example, in situ, real-time monitoring of carbon fiber characteristics. When the material composition is a carbon fiber tow, the present method may include adjusting process parameters of the carbon fiber production process if the specific property of the carbon fiber tow does not fall within a preferred specification range. If the material composition is not a carbon fiber tow, but rather a nylon fiber or some composite material, the present method may also include, for example, heating the material to control the moisture content. Such controlling may be performed with the use of a computer, among other things. For instance, this computer may be used to raise or lower the temperature in different steps of the production process if the portion of the carbon fiber tow fed through the resonance cavity does not fall within a given specification range.

In one embodiment of the present invention where the material composition is the carbon fiber tow, experimental measurements were made to determine the relationship between the loss tangent of carbon fiber and the intrinsic density of that carbon fiber. First, the dielectric properties (loss tangent) of a tow of carbon fibers having an approximately 60 foot continuous length were measured using the material composition monitor 8 identified in FIG. 2 to determine sections of the continuous length of the carbon fiber tow having a high loss and low loss, respectively. Discrete high and low loss regions of the continuous fiber length (about 2–3 inches in length) were measured to determine their intrinsic densities.

Although measurements of the intrinsic densities of these carbon fibers were made, these are not the only measurements that can be correlated to changes in the dielectric properties of that carbon fiber length. Experimental data has demonstrated that after each specific stage of carbon fiber production, carbon fiber exhibits non-uniform dielectric properties as a function of its fiber length, among other things. The dielectric property of a sample of carbon fiber tow will differ from one stage of the carbon fiber production process to the next. Dielectric properties are extremely sensitive to any minute variation in the morphology of carbon fibers, and measured dielectric properties correlate well with carbon fiber properties such as intrinsic density. As discussed above, dielectric properties are also extremely sensitive to, and correlate well with, changes in the moisture content, purity or composition of a carbon fiber or other material composition. The correlation of these values—dielectric properties and morphology indicates that a determination of dielectric loss as a function of carbon fiber length will further allow the identification of the intrinsic density of that carbon fiber length. For each individual precursor filament used to ultimately produce a carbon fiber using a specific carbon fiber production process, a baseline for the carbon fiber must be obtained by using a pre-experimentation run of carbon fiber and plotting a correlation between the dielectric properties of that carbon and some morphological characteristics of the carbon fiber, such as intrinsic density, among others. This correlation can then be used to form an algorithm for determining the correlation between these characteristics of the carbon fiber production in the future, and from this correlation a specification range can be set for the carbon fiber tows being produced. This algorithm and correlation and specific to the carbon fiber production process and precursor that were used to make the initial plot, and to the specific location in the production process in which the measurements are being made (i.e., oxidation, carbonization, graphitization).

The intrinsic density of the carbon fibers was measured using Micro-Ultra Pycnometry, which uses the principle of fluid/volume displacement to measure the density of the constituents of the carbon fiber. The working fluid used in this carbon fiber density measurement was helium. Density measured using this approach is highly accurate (up to 4-place accuracy) and repeatable with ±0.02% variation, which provides for a good correlation between intrinsic density and any minute change in carbon fiber morphology.

Morphological changes in the test length of carbon fibers were found using wide-angle x-ray diffractometry. The shape and peak height of the two designated regions of a x-ray diffractograms can be used to indicate subtle morphological changes in the carbon fibers. Differences in the morphological stages or levels of each of the discrete high and low loss regions of the continuous carbon fiber tow length can be identified from the differing x-ray diffractograms of each of these regions. These x-ray diffractograms can also be used to identify an approximate percentage of converted/stabilized base structural units (BSU), and their degree of ordering, in the discrete high and low loss regions of the continuous fiber length as a function of their production process stage. These measurements, as well as those made with respect to the intrinsic density of the test sample length of carbon fibers, confirm that the dielectric properties of a length of carbon fibers does correlate to the morphological inhomogeneity along that length of carbon fibers. This x-ray diffractometry is not used to determine the amount of lossiness of a given sample carbon fibers, but x-ray diffractometry can be used to make a relative comparison of adjacent sample carbon fibers to show that one sample carbon fiber has different morphological characteristics from the other sample carbon fiber. This comparison can even be established between sample carbon fibers on different carbon fiber tows (from the same precursor filament), as long as the samples are at the same production point (i.e., both sample carbon fibers have undergone the carbonization process).

Thus, measurement of the dielectric properties along the length of carbon fiber tow is sufficient to adequately monitor changes in the morphology of that tow and to thereby monitor and control a continuous carbon fiber manufacturing line.

FIG. 4 shows the correlation between the measured dielectric properties of the discrete high and low loss regions of a continuous fully oxidized polyacrylonitrile (PAN)-based fiber length and their intrinsic density and calculated area. Tan δ is the loss tangent or the dissipation factor, which is an indicator of how lossy the material is when subjected to an oscillating electromagnetic field. In the case of carbon fiber precursor morphology measurements, the loss tangent is one of the strongest indicators of the state of carbonization and graphitization, as it is proportional to the conductivity of the carbon fiber (which increases as the processing proceeds). Variations in the loss tangent on a continuously moving carbon fiber tow would directly indicate variations in carbonization along that carbon fiber tow.

The dielectric properties of the fiber samples which are generally determined, among others, using the resonance cavity technique are generally referred to as $\epsilon'$ and $\epsilon''$, where $\epsilon'$ is the real part of a complex dielectric constant and $\epsilon''$ is the "imaginary" part. The real part $\epsilon'$, refers is closely related to the change in wavelength of a wave (compared to a wave of the same frequency in a vacuum) and the imaginary part $\epsilon''$, is related to the attenuation of the wave in the dielectric due to losses caused primarily by collisions between rotating molecules in the dielectric and also electronic collisions. Tan δ is equivalent to the ratio of $\epsilon''$ to $\epsilon'$ (or $\epsilon''/\epsilon'$), and it identifies how lossy the carbon fiber tow is when subject to an oscillating electromagnetic field.

FIG. 4 also shows the indicated average tan δ and $\epsilon''$ over the complete evaluated test length samples in the evaluated completed carbon fiber tow. These indicated average tan δ and $\epsilon''$ are derived from the observed average electric quality factor (Q) of the resonance cavity during the evaluation. For the lowest order mode in a rectangular cavity (often referred to at TE101), the real part of the dielectric constant $\epsilon'$ is determined using this equation:

$$\epsilon' = \frac{(D_f \times V_c)}{(2 \times f_o \times A_s \times h)}$$

where $D_f$ is the shift in resonance frequency of the resonance cavity with the addition of the carbon fiber tow, $V_c$ is the resonance cavity volume, $f_o$ is the resonant frequency of the empty resonance cavity, $A_s$ is the cross sectional area of the carbon fiber tow, and h is the cavity height (and the length of fiber in the cavity). The imaginary part of the dielectric $\epsilon''$ is determined using:

$$\epsilon'' = \left(\frac{-fs}{2} \times Df\right) \times (\epsilon' - 1) \times \left(\frac{1}{Q_o} \times \frac{1}{Q_s}\right)$$

where $f_s$ is the resonant frequency of the resonance cavity with the carbon fiber tow present, $D_f$ is the shift in the resonant frequency from the resonant frequency of the empty resonance cavity, $\epsilon'$ is the given by the equation above, $Q_o$ is the electric quality factor of the empty resonance cavity and $Q_s$ is the electric quality factor of the resonance cavity with the carbon fiber tow present. The electric quality factor can be measured by $Q=f_c/d_f$ where $f_c$ is the resonant frequency (empty or filled) and $d_f$ is the "half-power" bandwidth of the transmitted signal through the cavity, and $f_o$ is given in the equation above.

The average intrinsic density and calculated tow area over the completely evaluated test length of carbon fiber tow is calculated by the simple arithmetic sum of all discrete intrinsic density and calculated tow area measurements divided by the number of discrete measurements that were made.

Corresponding x-ray diffractograms for sample numbers are shown in FIGS. 5, 6, 7, and 8. These x-ray diffractograms show that a low lossy carbon fiber region does not show a predominant first peak at 2 Theta angle of approximately 16 to 17 degrees. In this case, Theta is the Bragg angle. X-ray diffractograms, such as the one illustrated in FIG. 6, generally identify a low lossy carbon fiber region as having a flat response. In x-ray diffractograms showing a high lossy carbon fiber region, such as FIG. 6, this predominant first peak region characterizes unconverted, unpyrolized material that still needs to be transformed to oriented graphene carbon/graphite material. Two very well defined peaks in a x-ray diffractogram characterize a high lossy carbon fiber region.

Figure 8:
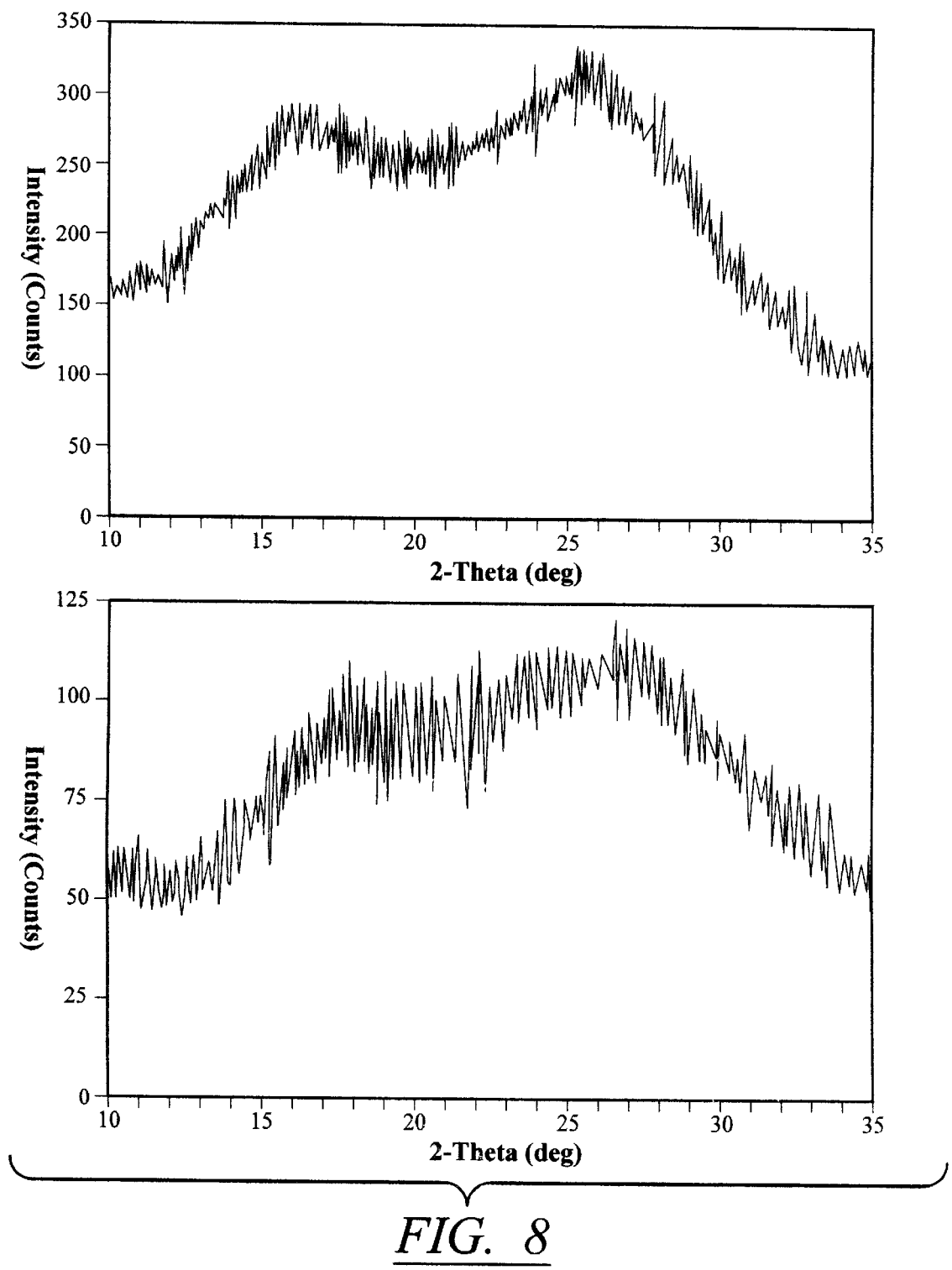
FIG. 8 is a comparison of x-ray diffractograms of, a second sample of highly lossy and a second sample of low lossy fully oxidized carbon fibers.

A comparison between x-ray diffractograms of a high lossy (sample 4 in FIG. 4) and low lossy (sample 1 in FIG. 4) fully oxidized carbon fiber region are shown in FIG. 8. In comparing these two x-ray diffractograms to one another, it ban be determined that the sample carbon fiber segments associated with the corresponding x-ray diffractograms of FIG. 8 will have different morphological states. Furthermore, FIG. 4 identifies that these sample carbon fiber segments have different values for tan δ, such that the highly lossy (sample 4, which corresponds to the top x-ray diffractogram) sample carbon fiber has a tan δ=0.4711 and the low lossy (sample 1, which corresponds to the bottom x-ray diffractogram) sample carbon fiber has tan δ=0.0221. This difference in tan 67 further illustrates that the highly lossy and lowly lossy sample carbon fiber segments will have different morphological states. FIG. 4 illustrates that this is indeed correct, as the intrinsic density of the highly loss sample carbon fiber (sample 4) is 1.4364 gr/cc, while the intrinsic density of the lowly lossy sample carbon fiber (sample 1) is 1.4126 gr/cc. Thus, these differences in the dielectric properties of carbon fiber tows can be used to determine relative variations in the morphology of those carbon fiber tows.

It is important to acknowledge that in comparing the discrete samples identified in FIG. 4 evaluated properties (e.g., tan $\delta$, intrinsic density, x-ray diffractograms, etc.) of these samples may only be relatively compared against adjacent samples on the test carbon fiber length. For the purposes of the present invention, however, the differences between sample groups will be irrelevant because the maximum and minimum fiber quality acceptances for each aspect of the carbon fiber production process will be known.

FIG. 9 shows the correlation between the measured dielectric properties of the discrete high and low loss regions of a carbonized PAN-based fiber length and their intrinsic density and calculated area. As in FIG. 4, only adjacent samples of FIG. 9 (i.e., samples 1 and 2, samples 3 and 4, etc.) can be relatively compared with any meaning. From the observed values of tan 67 , it appears that these carbonized fibers are more dielectrically homogeneous than the fully oxidized fiber samples illustrated in FIG. 4. Samples of dielectrically high loss are more infrequent and less abundant, which corresponds to the general low loss characteristics of fibers during the carbonization stage. The observed average values of tan $\delta$ and $\epsilon''$ along the evaluated tow length is closer to the low loss level and the observed high loss appears rather sporadically. The range of variation of the dielectric properties for this stage of processing was observed to be considerably narrower than fibers after the stabilization (oxidation stage).

Figure 10:
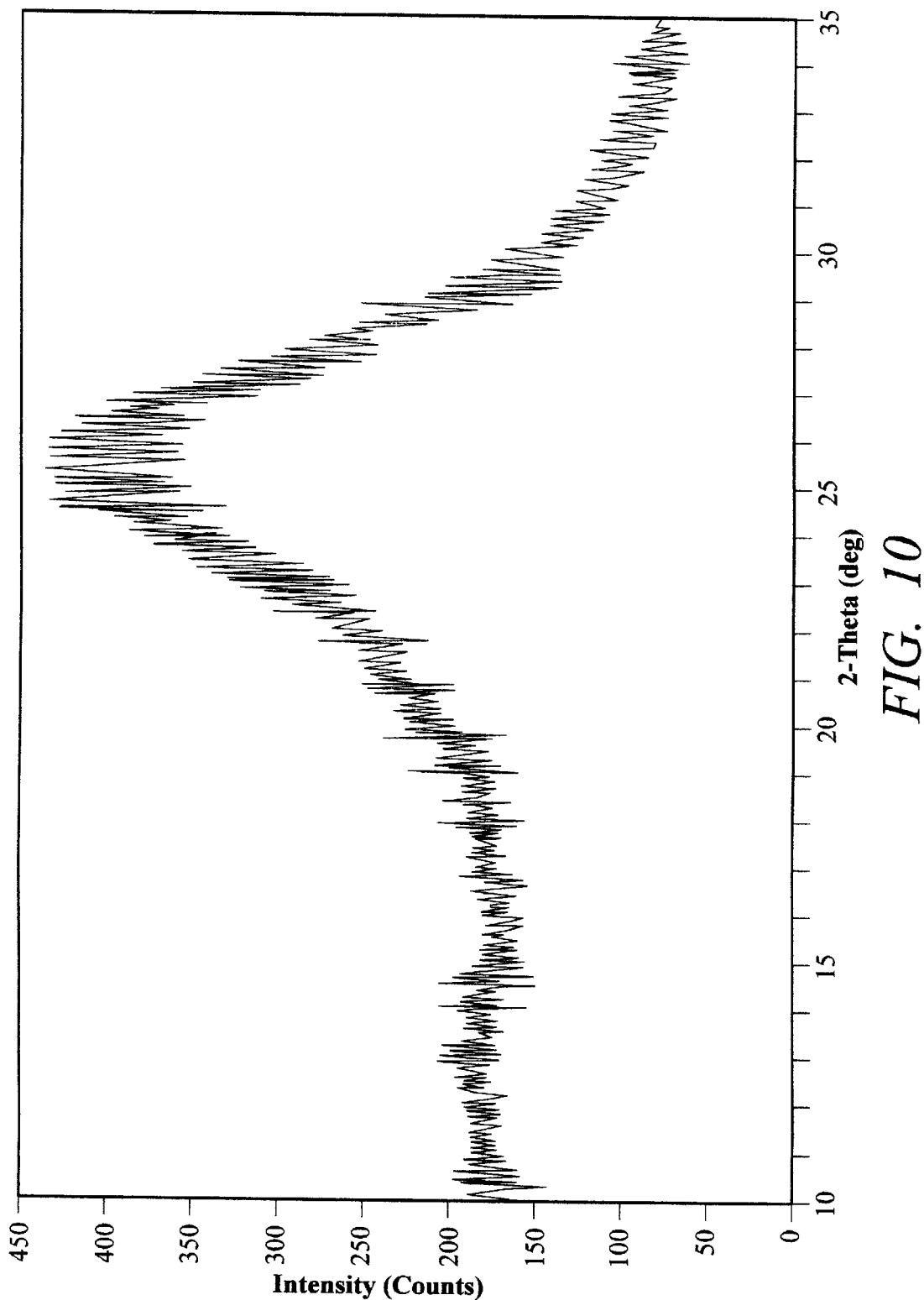
FIG. 10 is an x-ray diffractogram illustrating the intensity of low lossy fully carbonized PAN-based carbon fibers.
Figure 11:
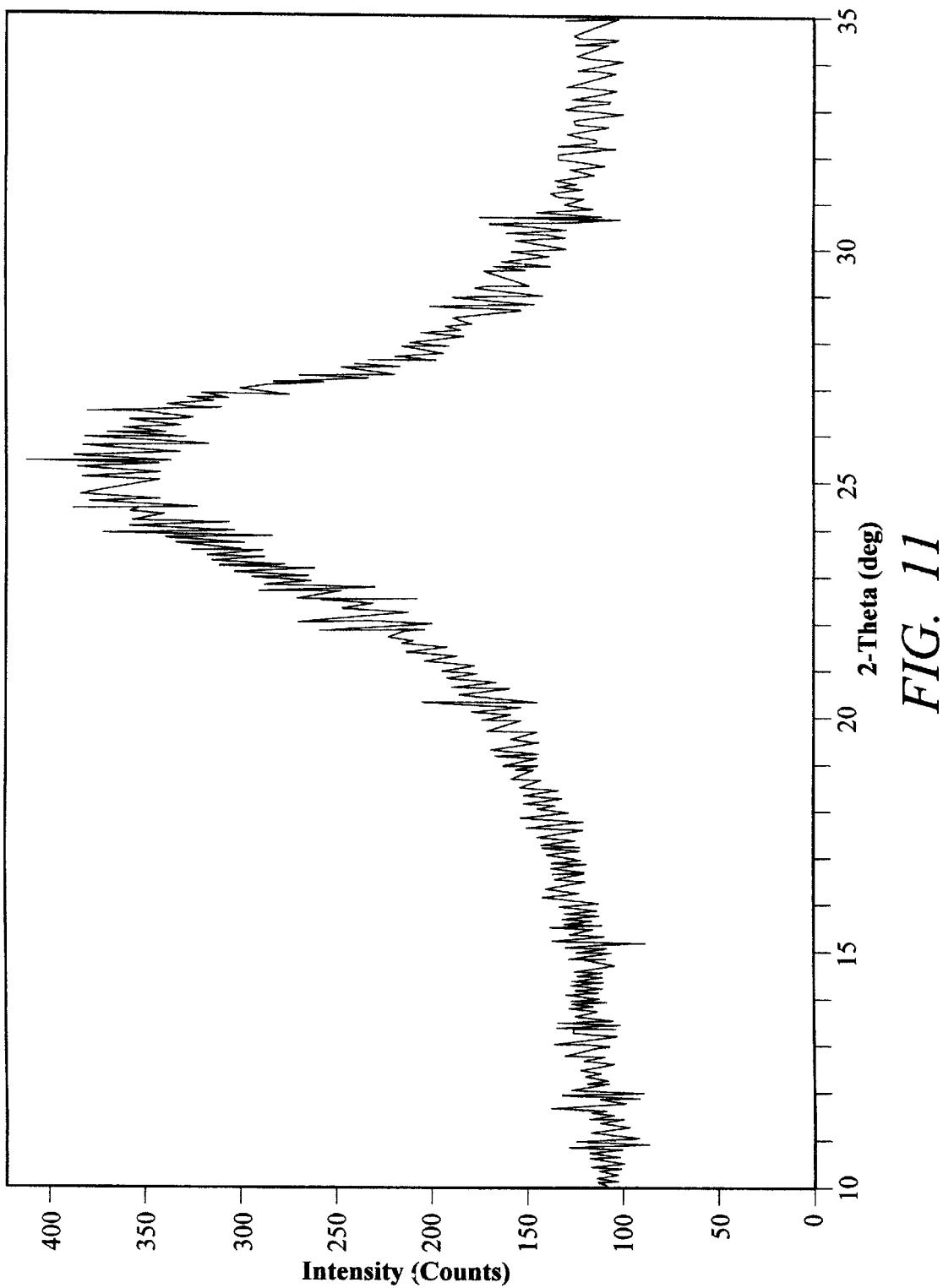
FIG. 11 is an x-ray diffractogram illustrating the intensity of highly lossy fully carbonized PAN-based carbon fibers.

FIGS. 10 and 11 represent x-ray diffractograms of low loss and high loss regions of the evaluated tow length, respectively. The initial portion of the diffractogram curve (between 10 and 20 degrees 2 Theta) of FIG. 10 (low loss sample) shows a higher intensity level (in counts) than that shown in the same portion of FIG. 11 (high loss sample). This higher intensity level suggests that there is a higher fraction of unconverted material (thermoplastics) in the low loss region that still requires conversion than there is in the high loss region, because virgin polyacrylonitrile thermoplastic material demonstrated very low dielectric coupling when subjected to an oscillating electromagnetic field.

In order for the present invention to properly monitor and control the carbon fiber production process, the correlation between the values of the dielectric properties of a carbon fiber and the characteristics or morphology of that carbon fiber is preferably known. This requires a "base-line" of the interrelation for these two properties to be constructed as a function of each individual production stage and as a function of each specific precursor material that will be used. As it has already been established that there are definite relationships between dielectric measurements and mechanical properties, such as intrinsic density, mechanical strength, ultimate strength, elasticity models, tensile strength, etc., as well as one between mechanical properties and carbon fiber morphology and the degree of that fiber's material transformation, these values can be used to form the required base-line correlation defined above. Additional data and statistical analysis of this data may be used to develop the mathematical relationship between these properties. Once this relationship is fully defined, an algorithm may be developed for continuously monitoring the process and providing feedback to a controller for controlling changes or modifications made to the production process based on the monitored real-time material assessments that are made.

Figure 12:
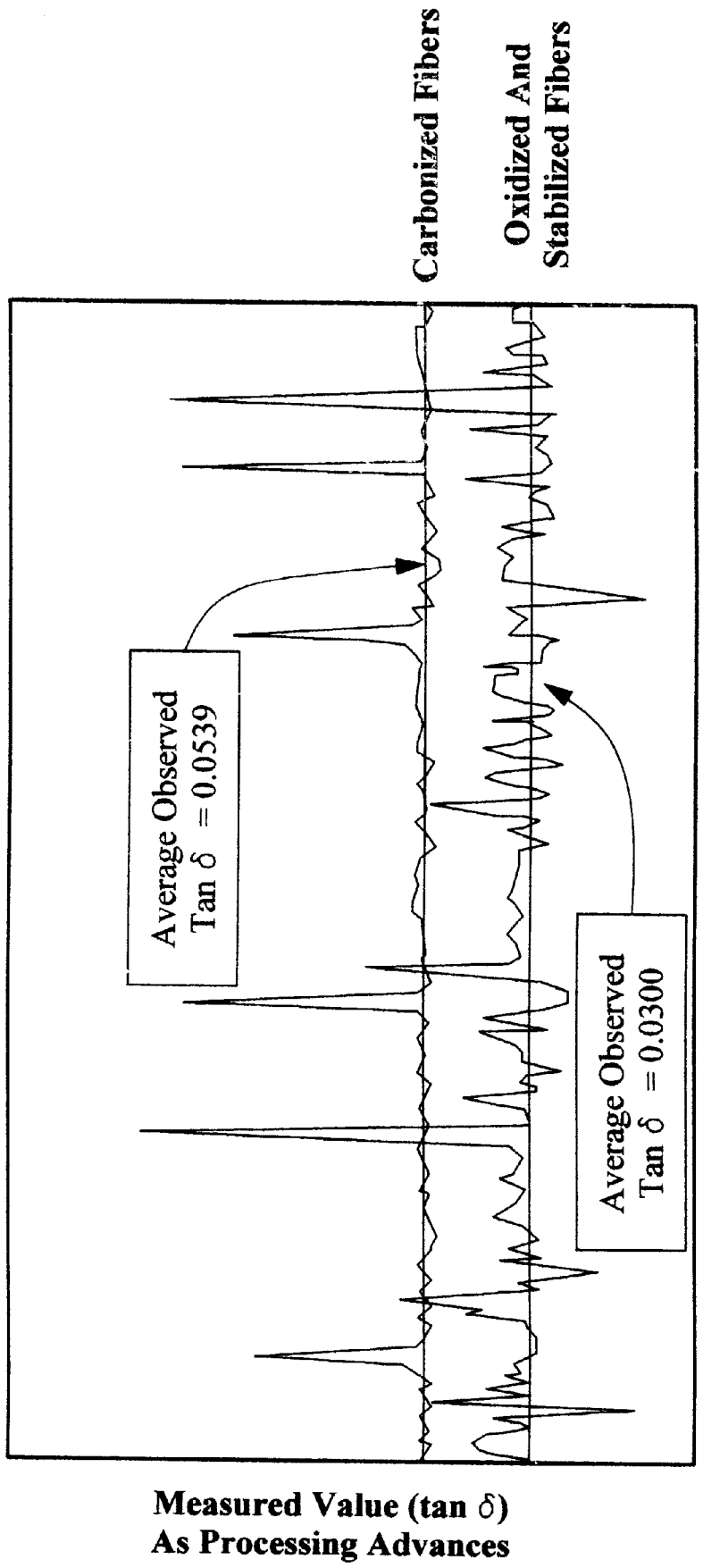
FIG. 12 is an illustration of the measured values of the loss tangent along a carbon fiber length as a function of production stages.

From the monitoring of the test length of carbon fiber tow, it has been ascertained that the observed average coupling characteristics (e.g., Tan $\delta$) to the incident electromagnetic field increases with the advancement of the processing of a given carbon fiber tow. For example, the average tan $\delta$ value after stabilization was 0.0300, whereas the average tan $\delta$ value after carbonization was 0.0539. Also observed was the narrowing of the spread or variation of tan $\delta$ values with the advancement of the processing of a given carbon fiber tow. For example, the variation in tan $\delta$ values for the fully carbonized samples of carbon fiber where very narrow compared to the variation for early processing stages, such as full oxidation (illustrated in FIG. 4). FIG. 12 schematically represents the sensitivity of tan $\delta$ values to a given length of carbon fiber for each stage, and thus its suitability as a monitoring or controlling method for industrial applications.

In an alternative embodiment of the present invention, the method described above can alternatively be used to identify the purity, quality, composition, or moisture content of materials. For example, the measured dielectric properties of materials can be used to identify changes or modifications in the purity, quality, composition, or moisture content of those materials.

Referring to FIG. 13, a table illustrating the correlation between the dielectric properties of a given substrate and the moisture content of that substrate, according to the present invention, is illustrated. This table illustrates that there is a difference between the dielectric properties of a moist substrate and the dielectric properties of that same substrate after it is dried. This table identifies the dielectric properties of the substrate as a function of the $\epsilon'$ and the tan $\delta$ values of the substrate. As defined above, $\epsilon'$ is the real part of the complex dielectric constant of the substrate, while tan $\delta$ is the loss tangent or the dissipation factor of the substrate. This tan $\delta$ is an indicator of how lossy the substrate is when subjected to an oscillating electromagnetic field.

In FIG. 13, the tested substrate is commercial grade glass-fiber/epoxy reinforced composite (GFRC). According to this embodiment of the present invention, the material monitor used to determine the properties of a material will generally have a resonance cavity using lower frequency microwaves. As with the alternative embodiment of the invention discussed previously herein, these lower frequency microwaves are preferably in the S-Band frequency range (in the range of 2 GHz to 4 GHz). For example, the resonance cavity used in the material monitor to determine the moisture content of the GFRC in FIG. 13 had a frequency of 2.44 GHz.

Figure 14:
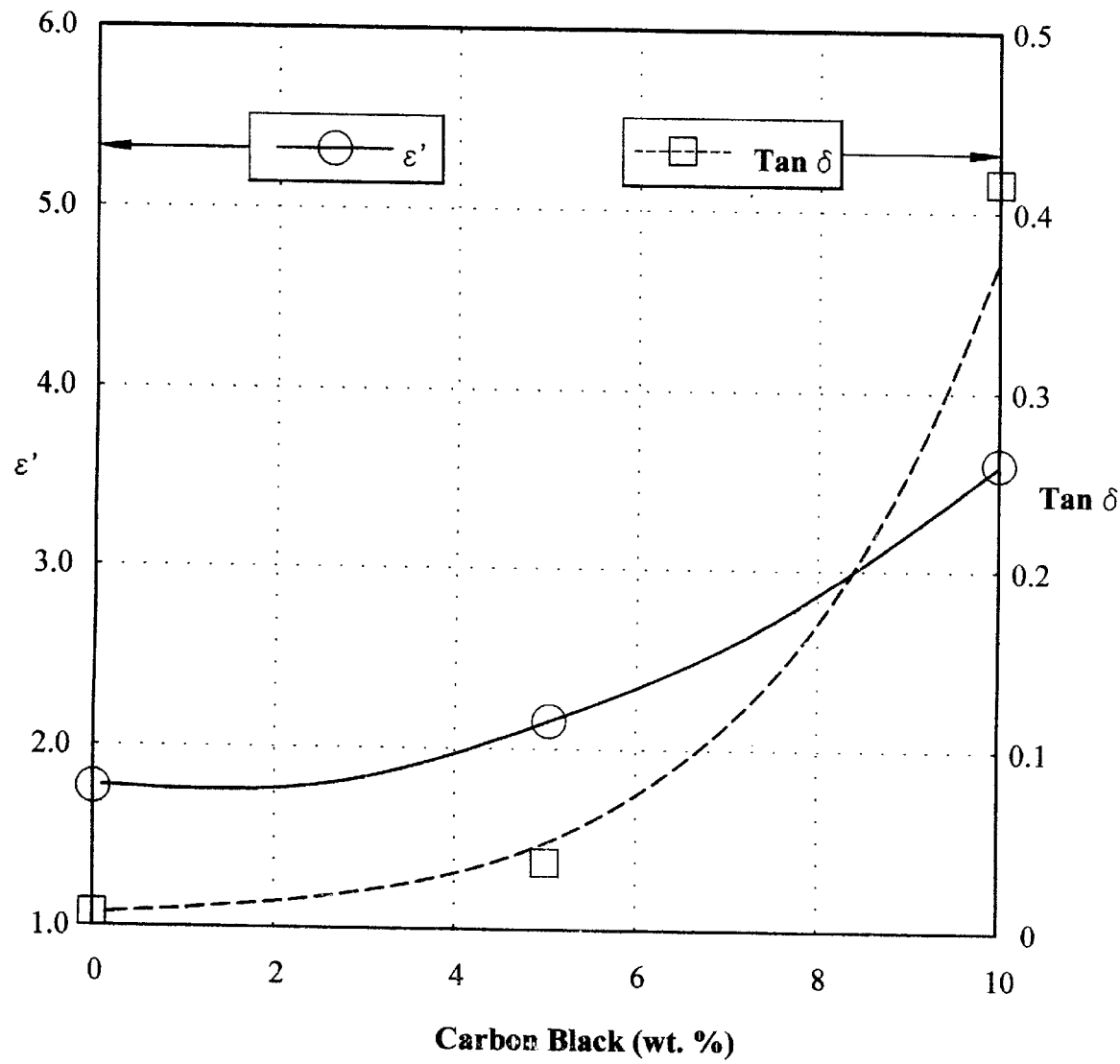
FIG. 14 is a graph illustrating the correlation between the dielectric properties of a polyamide, nylon product and the percentage by weight of carbon black additive present in the polyamide, nylon product.

Referring to FIG. 14, a graph illustrating the correlation between the dielectric properties of a given substrate and the composition of that substrate, according to the present invention, is illustrated. This graph illustrates the change in dielectric property of a material composition as the percentages of materials changes within that composition. This graph identifies the dielectric properties of the material composition as a function of the $\epsilon'$ and the tan $\delta$ values of that composition.

In FIG. 14, the material composition contains both DSM KS-200 and carbon black additives. KS-200 is a specific manufacture of polyamide, nylon (PA 4/6). This thermoplastic polymer is produced by DSM Engineering Plastic Products, Inc. of Reading, Pa. The table identifies DSM KS-200 as a function of the percentage of weight of the material composition composed of carbon black additives. For example, according to FIG. 14, pure DSM KS-200 has a tan δ of around 0 and a ε' of around 1.9. When ten percent of the weight of DSM KS-200 is composed of carbon black additive, the tan δ of the DSM KS-200 increases to around 0.375 and the ε' of the DSM KS-200 increases to around 3.5. These increases are curvilinear in nature, and identify a continuous increase of both tan δ and ε' values in DSM KS-200 as a function of an increased percentage of carbon black additives. Thus, these dielectric properties can be used to determine whether there is a larger or smaller amount of carbon black additives present in a DSM KS-200 material composition.

As illustrated in FIGS. 13–14, these changes in dielectric properties can be used to determine the moisture content or composition in a material. Additionally, the same method of measuring changes in the dielectric properties of a material can further be used to measure the purity or quality of that material. As discussed previously herein, the changes in dielectric properties of materials identified in FIGS. 13–14 can be used to determine the moisture content of a given material, rather than whether that material is more or less moist. Furthermore, this method can be used to determine the percentage makeup of a given material within a material composition, rather than whether there is more or less of a material in that composition.

In order for the present invention to properly monitor the characteristics of material compositions, the correlation between the values of the dielectric properties of a material composition and the monitored characteristics, such as moisture content, purity or composition, of the material composition is preferably known. This requires a "baseline" of the interrelation for these two properties to be constructed as a function of each specific material composition, as well as each specific characteristic, that is desired to be monitored. As it has already been established that there are definite relationships between dielectric measurements and properties, such as moisture content, composition and purity, among other things, these values can be used to form the required base-line correlation defined above. Additional data and statistical analysis of this data may be used to develop the mathematical relationship between these properties. Once this relationship is fully defined, an algorithm may be developed for continuously monitoring the characteristics of the material compositions. The information from this algorithm can then be used for providing feedback for controlling changes or modifications made to whatever processing of the material composition is being monitored. For example, if a material composition is being dried for use in a later manufacturing process, the information from the algorithm can be used for controlling the amount of heat applied to the material composition so that the desired moisture content of the material composition can be achieved.

It should be understood that the examples and embodiments described herein are for illustrative purposes only and that various modifications or changes in light thereof will be suggested to persons skilled in the art and are to be included within the spirit and purview of this application.

The invention can take other specific forms without departing from the spirit or essential attributes thereof for an indication of the scope of the invention.

What is claimed is:

1. A method for monitoring characteristics of materials, comprising the steps of:
    placing a material in an application zone;
    applying microwave energy to said application zone to produce a microwave field within said application zone;
    measuring at least one microwave parameter related to said microwave field;
    determining a change in said microwave parameter caused by the presence of said material in the application zone; and
    relating said change in said microwave parameter caused by said placing of the material in the application zone to at least one desired dielectric characteristic of the material.

2. The method according to claim 1, wherein the step of placing the material in the application zone further comprises feeding the material through the application zone.

3. An apparatus for monitoring characteristics of materials, comprising:
    a microwave energy source for producing a microwave field within an application zone;
    a measurer for measuring at least one microwave parameter related to said microwave field resulting after placing a material in the application zone; and
    a processor for relating said changes in said microwave parameter caused by placing the material in the application zone to at least one desired dielectric characteristic of the material.

4. The apparatus according to claim 3, further comprising a placement device for placing the material in the application zone, wherein the placement device for placing the material in the application zone is a feeder for feeding the material through the application zone.

5. A method for producing carbon fiber tows, comprising the steps of:
    transporting a multiplicity of filaments through production stages,
    wherein said production stages further comprise the steps of:
        pretreating a multiplicity of filaments;
        oxidizing said pretreated multiplicity of filaments;
        carbonizing said oxidized multiplicity of filaments;
        graphitizing said carbonized multiplicity of filaments; and
        treating the surface of the graphitized multiplicity of filaments; and
        monitoring the properties of the multiplicity of filaments at least once during said transporting of the multiplicity of filaments through production stages, wherein said monitoring of the multiplicity of filaments further comprises the steps of:
        placing a multiplicity of filaments in an application zone;
        applying microwave energy to produce a microwave field within said application zone;
        measuring changes in at least one microwave parameter related to said microwave field by said placing of the multiplicity of filaments in the application zone; and
        relating said changes in said microwave parameter caused by said placing of the multiplicity of filaments in the application zone to at least one desired dielectric characteristic of the multiplicity of filaments.

6. The method according to claim 5, wherein the step of transporting the multiplicity of filaments through the production stage is noncontinuous.

7. The method according to claim 6, wherein the step of placing a multiplicity of fibers in the application zone further comprises the step of feeding the multiplicity of fibers through the application zone.

8. A method for producing carbon fiber tows according to claim 7, further comprising the step of sizing and drying the treated multiplicity of filaments.

9. An apparatus for producing carbon fiber tows, comprising:
- a transporter for transporting a multiplicity of precursor filaments through the carbon fiber production process;
- a pretreater for preparing the multiplicity of precursor filaments for oxidation;
- an oxidizer for oxidizing the multiplicity of precursor filaments transported by said transporter from said pretreater;
- a carbonizer for carbonizing the oxidized multiplicity of filaments transported by said transporter from said oxidizer;
- a graphitizer for graphitizing the carbonized multiplicity of filaments transported by said transporter from said carbonizer;
- a treater for treating the surface of the graphitized multiplicity of filaments transported by said transporter from said graphitizer; and
- at least one single mode resonant cavity monitor for monitoring the morphology of the multiplicity of filaments transported by said transporter in at least one position through the carbon fiber production process, said resonant cavity monitor including a microwave energy source for producing a microwave field within said resonant cavity, a measurer for measuring at least one microwave parameter related to said microwave field, said microwave parameter being a function of said morphology of said multiplicity of filaments; and a processor for relating said changes in said microwave parameter to said morphology of said multiplicity of filaments.

10. The apparatus according to claim 9, wherein the transporter non-continuously transports the multiplicity of filaments through said resonant cavity monitor.

11. The method of claim 1, wherein the application zone is a resonant cavity.

12. The method of claim 1, wherein the resonant cavity is a microwave resonant cavity.

13. The method of claim 1, wherein the material comprises at least one tow.

14. The method of claim 1, further comprising the step of measuring said microwave parameter prior to placing the material in the application zone.

15. The apparatus according to claim 3, wherein the application zone is a resonant cavity.

16. The method of claim 5, wherein the application zone is a resonant cavity.

17. The method of claim 5, further comprising the step of measuring said microwave parameter prior to placing the material in the application zone.

18. The apparatus according to claim 9, wherein the transporter continuously transports the multiplicity of filaments through said resonant cavity monitor.

19. The apparatus according to claims 15, wherein said resonant cavity is a single mode resonant cavity.

20. The method according to claim 1, wherein said material is a dielectric material, further comprising the step of relating said dielectric characteristic to at least one specific property of said material, said specific property being at least one selected from the group consisting of moisture-content, purity, composition, intrinsic density, mechanical weight, and ultimate strength.

* * * * *